United States Patent [19]

Gold et al.

[11] Patent Number: 4,622,200
[45] Date of Patent: Nov. 11, 1986

[54] NON-DESTRUCTIVE METHOD FOR DETERMINING NEUTRON EXPOSURE AND CONSTITUENT CONCENTRATIONS OF A BODY

[75] Inventors: Raymond Gold; William N. McElroy, both of Richland, Wash.

[73] Assignee: The United States of America as represented by the United States Department of Energy, Washington, D.C.

[21] Appl. No.: 582,510

[22] Filed: Feb. 22, 1984

Related U.S. Application Data

[63] Continuation-in-part of Ser. No. 547,681, Jan. 1, 1983, abandoned.

[51] Int. Cl.$^4$ ............................................. G21C 17/00
[52] U.S. Cl. ................................... 376/159; 376/245; 250/370
[58] Field of Search ................................ 376/153–155, 376/159, 245, 257; 250/369, 370, 390–392, 370 R, 370 F, 370 E, 371, 395, 358.1; 378/155

[56] References Cited

U.S. PATENT DOCUMENTS

| | | | |
|---|---|---|---|
| 2,998,550 | 8/1961 | Collins et al. | 250/370 |
| 3,043,955 | 7/1962 | Friedland et al. | 250/370 |
| 3,225,196 | 12/1965 | Gigon et al. | 250/391 |
| 3,311,770 | 3/1967 | Boyd | 376/154 |
| 3,483,376 | 12/1969 | Locke et al. | 250/392 |
| 3,496,357 | 2/1970 | Weinzierl et al. | 376/159 |
| 3,527,944 | 9/1970 | Kraner | 250/370 |
| 3,612,869 | 10/1971 | Baum et al. | 250/370 |
| 3,717,765 | 2/1973 | Hiller | 376/257 |
| 3,786,253 | 1/1974 | Haffner et al. | 250/390 |
| 4,090,072 | 5/1978 | Michaelis et al. | 376/159 |
| 4,152,596 | 5/1979 | Marshall, III | 376/159 |
| 4,203,037 | 5/1980 | Gur et al. | 378/155 |
| 4,345,153 | 8/1982 | Yin | 250/369 |
| 4,483,817 | 11/1984 | Evans et al. | 376/154 |

OTHER PUBLICATIONS

Gold, "Estimates of High Energy Gamma and Neutron Flux from Continuous Gamma Ray Spectrometry", LWR Pressure Vessel Irradiation Surveillance Quarterly Progress Report (9/78), NUREG/CR-0551, pp. HEDL-37–HEDL-48.
Gold, "Compton Recoil Gamma Ray Spectroscopy", Nuc. Instr, Meth, vol. 85, pp. 173–194 (1970).
Gold et al, EUR6813, vol. II, pp. 1160–1170 (1980) "Reactor Gamma Ray Spectroscopy: Status".
Kaiser et al, "Gamma Ray Spectrometry", LWR Pressure Vessel Surveillance Dosimetry Improvement Program, NUREG/CR-1861, pp. 5.2-1–5.2-34 (1981).
Gold et al, "Gamma Ray Spectrometry in LWR'S", 4th Int. ASTM-Euratom Symposium on Reactor Dosimetry, NBS. Wash, D.C. (3182).
McNeece et al, HEDL-7285 (1983).
McElroy et al, Sec 2.4.1 NUREG/CR-2805, vol. 3 (1983).

*Primary Examiner*—Salvatore Cawgialosi
*Attorney, Agent, or Firm*—Edward W. Nypaver; Robert Southworth, III; Judson R. Hightower

[57] ABSTRACT

A non-destructive method for determination of neutron exposure and constituent concentrations in an object, such as reactor pressure vessel, is based on the observation of characteristic gamma-rays emitted by activation products in the object by using a unique continuous gamma-ray spectrometer. The spectrometer views the object through appropriate collimators to determine the absolute emission rate of these characteristic gamma-rays, thereby ascertaining the absolute activity of given activation products in the object. These data can then be used to deduce the spatial and angular dependence of neutron exposure or the spatial constituent concentration at regions of interest within the object.

10 Claims, 2 Drawing Figures

NON-DESTRUCTIVE METHOD FOR DETERMINING NEUTRON EXPOSURE AND CONSTITUENT CONCENTRATIONS OF A BODY

The U.S. Government has rights in this invention pursuant to Contract No. DE-AC 14-76FF02170 between the U.S. Department of Energy and Westinghouse Electric Corporation.

CROSS-REFERENCE TO A RELATED APPLICATION

This application is a continuation-in-part of application Ser. No. 547,681, filed Jan. 1, 1983, on a Non-Destructive Method for Determining Neutron Exposure, and now abandoned.

BACKGROUND OF THE INVENTION

The present invention relates generally to a method for determining the neutron exposure and the constituent concentrations of an object such as a reactor pressure vessel. It is a radiometric technique based upon the fact that such neutron exposure induces radioactivity in the form of characteristic gamma-rays.

This disclosure relates specifically to a system originally developed for determination of reactor pressure vessel neutron exposure by a non-destructive technique. Such determinations are important in ascertaining the projected useful life of an active nuclear reactor. This non-destructive technique is an alternative to conventional techniques for directly counting activity in a sample area that is physically removed from the pressure vessel.

The present method of neutron dosimetry utilizes available continuous gamma-ray spectrometry techniques in a specialized physical application to achieve an effective non-destructive testing process for the nuclear industry A portable probe having a specially shielded detector is partially exposed to one or more surfaces through a collimator opening that is directed toward the surface area being tested. By measuring the resulting continuous spectrum of detected gamma-rays at different energy levels and recording one or more flux density peak values of the gamma-rays at energy levels characteristic of neutron exposure, one can mathematically derive a relationship between the flux density peak values and the spatial activity density. However, since this relationship will also include a second unknown—the neutron attenuation coefficient of the object being tested—it is necessary to either conduct separate tests to measure the neutron attenuation coefficient, or to make another set of measurements with a different collimator arrangement at a second solid angle and then mathematically solve the resulting relationships to determine the two unknown quantities expressed within them. Once the spatial activity density value of gamma-rays at the characteric energy levels is identified, one can deductively derive information concerning the spatial distribution of the neutron exposure by using known relationships between spatial activity density values and neutron exposure.

A general discussion of the Compton effect in lithium-drifted germanium detectors utilized in gamma spectroscopy can be found in U.S. Pat. No. 3,612,869 and in U.S. Pat. No. 3,527,944. A collimated radiation assembly to sequentially expose portions of an object to X-ray radiation is disclosed in U.S. Pat. No. 4,203,037. Other U.S. Patents of general background interest with regard to this invention are U.S. Pat. Nos. 3,483,376; 4,345,153; 2,998,550; 3,786,253; 3,043,955; 3,225,196; and 3,311,770.

It should also be appreciated that the embrittlement of reactor pressure vessel steels is a significant factor in determining the expected useful life of the pressure vessel. Because weldments are generally the weakest regions in such vessels, their anticipated life usually governs the productive life of the vessel. Since copper is a crucial variable contributing to radioactive induced embrittlement of steel bodies, the capability of nondestructively determining or measuring the copper concentration in the pressure vessel base metals, and more particularly in the weldments thereof, becomes highly desirable. The present invention, in addition to providing a method for non-destructively determining the neutron exposure of irradiated bodies, also can be utilized to measure the copper concentration, as well as other constituent concentrations, of the pressure vessel base metals and weldments.

SUMMARY OF THE INVENTION

It is an object of this invention to provide an effective non-destructive method for measuring neutron exposure about an object by use of a portable detector that eliminates the need for physically sampling the structure of the object.

It is another object of this invention to provide an effective method for utilizing known interrelationships between the gamma-ray and neutron components of the mixed radiation field typically encountered in reactor environments in order to permit gamma-ray measurement techinques to serve indirectly as neutron exposure measurement techniques.

It is a further object of the present invention to utilize the foregoing non-destructive neutron exposure determination method for additionally measuring the concentrations of different constituents in an irradiated object of interest.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects and in accordance with the purposes of the present invention •as embodied and broadly described herein, the process of this invention basically comprises the steps of exposing a gamma-ray detector to a limited portion of the surface area of the object through a collimater opening, electronically measuring the spectrum of detected gamma-rays at different energy levels, recording the flux density peak value at a selected energy level characteristic of neutron exposure; identifying the spatial activity density from its relationship to the measured flux density peak value, and deriving information concerning neutron exposure by making use of its known relationship to the identified spatial activity density value.

In a further aspect of this invention, in accordance with its objects and purposes, the foregoing non-destructive neutron exposure determination method also can be used for measuring constituent concentrations in the irradiated object by quantifying peaks in the gamma-ray spectrum due to activation of such constituents, respectively.

BRIEF DESCRIPTION OF THE DRAWINGS

The accompanying drawings, which are incorporated into and form a part of this specification, illustrate an embodiment of the present invention and, together with the description, serve to explain the principles of the invention. In the drawings.

DETAILED DESCRIPTION OF THE INVENTION

Figures 1, 2:
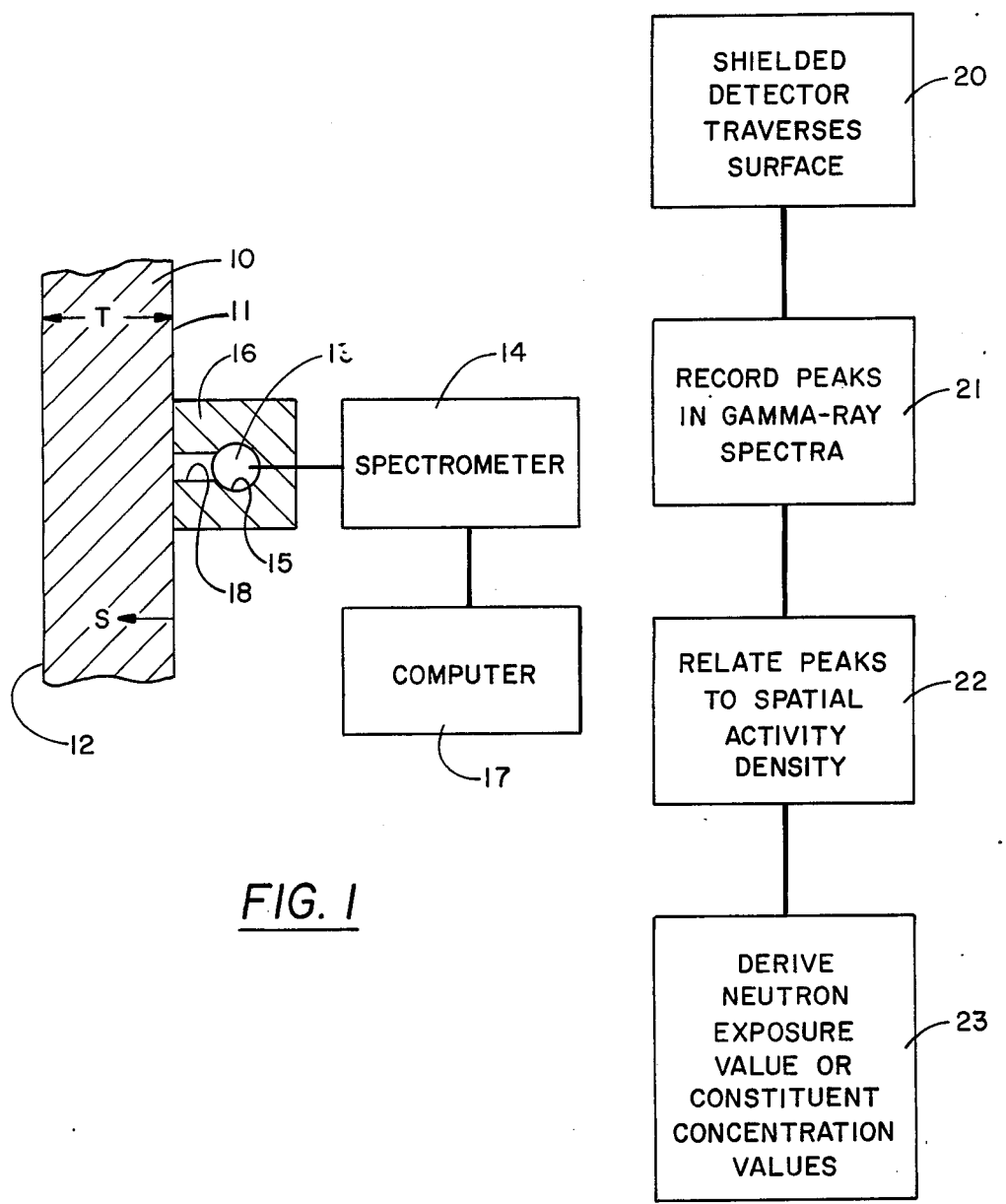
FIG. 1 is a schematic view of the apparatus used in the practice of the method.
FIG. 2 is a simplified flow diagram of the method steps.

The following publications and excerpts are hereby incorporated into this disclosure by reference:

A general description of the ability to conduct neutron dosimetry through continuous gamma-ray spectrometry was advanced in an article by R. Gold, "Estimates of High Energy Gamma and Neutron Flux from Continuous Gamma-Ray Spectrometry," *LWR Pressure Vessel Irradiation Surveillance Dosimetry Quarterly Progress Report*, July–September 1978, NUREG/CR-0551, HEDL-TME 78-8, Hanford Engineering Development Laboratory, Richland, Wash. pp. HEDL37-HEDL48 (1979).

The complementarity of the components of a mixed radiation field was introduced in an article by R. Gold, "Compton Recoil Gamma-Ray Spectroscopy," *Nucl. Instr. Methods* Vol 84, pp 173–194 (1970). In particular for mixed radiation fields in a reactor environment, the neutron and gamma-ray components possess a strong relationship. This interrelationship is manifested through the existence of intense gamma-ray peaks above the gamma continuum at characteristic and identifiable gamma-ray energies.

The ability to measure complex gamma-ray continua in reactor environments through Compton Recoil Gamma-ray spectrometry has been well established, as evidenced by the following papers:

R. Gold and B. J. Kaiser, "Reactor Gamma Spectrometry: Status", *Proceedings of the Third ASTM-Euratom International Symposium on Reactor Dosimetry*, Ispra (Varese), Italy, Oct. 1–5, 1979, EUR 6813, Vol II, 1160 (1980). (Invited Paper);

R. Gold and B. J. Kaiser, Gamma-Ray Spectrometry, W. N. McElroy, Ed., *LWR Pressure Vessel Dosimetry Improvement Program: PCA Experiments and Blind Test*, NUREG/CR-1861, p. 5.2-1-34 (1981);

R. Gold, B. J. Kaiser, and J. P. NcNeece, "Gamma-Ray Specrtrometry in Light Water Reactor Environments," *Fourth ASTM EURATOM International Symposium on Reactor Dosimetry*, NBS, Washington, D.C., March 1982 (invited paper).

Recent work for reactor recovery at Unit 2 of the Three Mile Island Reactor has demonstrated that the unique Compton gamma-ray spectrometer described in the above papers can be operated in very intense gamma fields. In fact, these efforts demonstrated that fields of up to roughly 2000 R/hr can be accommodated, using shielded collimaters of appropriate design. This work is described in the report: J. P. McNeece, B. J. Kaiser, R. Gold, and W. W. Jenkins, "Fuel Assessment of the Three Mile Island Unit 2 Makeup Demineralizers by Continuous Gamma-Ray Spectrometry", HEDL-7285 (1983).

The significance of copper in reactor pressure vessel steels is discussed in an article by W. N. McElroy et al, "LWR Pressure Vessel Surveillance Dosimetry Improvement Program", 1982 Annual Report, Section 2.4.1, NUREG/CR-2805, Vol. 3, HEDL-TME 82-20 (1983).

FIG. 1 schematically shows the configuration of an apparatus for carrying out this techinque with respect to an object exposed to neutron bombardment, such as the wall of a reactor pressure vessel. A selected wall structure 10 having opposite wall surfaces 11 and 12 is shown as having a wall thickness T. The solid state lithium-drifted silicon detector 13 of the Compton Recoil Gamma-Ray Spectrometer 14 is positioned within a complementary cavity 15 of a suitable shield 16 used to reduce overall gamma intensity to a few R/hr. The shield 16 will be typically constructed of lead. The spectrometer 14 is operatively connected to a computer 17 programmed to carry out the computational and deductive steps described below.

The shield 16 has a collimator opening 18 formed through one side of it and facing a surface of the object being tested. In a typical structure, the shield 16 will have a cylindrical external shape, and will be provided with a small diameter cylindrical collimator opening intersecting the center of the detector 13. The opening 18 can be coaxial with the cylindrical outer surface of the shield, or can be offset from such axis, depending upon the nature of the background radiation levels desired in the gamma-ray measurement steps.

FIG. 2 generally shows the method as a flow diagram. The uppermost box 20 is indicative of the step of scanning or traversing the surface 11 or 12 by the shielded detector 13, with the detector 13 being partially exposed to the surface area through the collimator opening 18. The next box 21 indicates that the peak values in the gamma-ray spectra are recorded. The recorded values at energy levels characteristic of radiation resulting from neutron exposure can then be selected for further processing. Box 22 indicates the step of relating the selected peak value information through known mathematical relationships to spatial activity density. Box 23 indicates the step of deducing or deriving neutron exposure values or constituent concentration values from the spatial activity density information.

The present method comprises a new and unobvious application of the very general concepts described in the referenced publications to a practical procedure for non-destructive evaluation of neutron exposure in an object such as a reactor pressure vessel wall. For reactor pressure vessel neutron dosimetry, the reactor would normally be shut down during testing. Measurements could be conducted on both sides of the wall, depending on accessibility. For example, on the core side of the reactor pressure vessel, one could place the shielded Compton spectrometer detector in a corner fuel assembly location, so as to measure the maximum exposure experienced by the reactor pressure vessel walls. Measurement on the other side, for instance in the reactor cavity, would have the advantage of reduced background.

Although not discussed specifically herein, the application of this method to measurements during low-power start-up, or possibly high power operation, are not excluded from this invention disclosure. The main difference here would be the observation of neutron induced capture E-rays from the iron and constituent elements of interest.

In carrying out such tests using the apparatus generally shown in FIG. 1, the detector 13 views the wall structure 10 through the collimator opening 18, which possesses a gap of diameter $d_1$ and a length $x_1$. The absolute flux intensity of a characteristic gamma-ray observed at energy $\epsilon_o$ which is expressed as $I_1(\epsilon_o)$ is given by the following equation:

$$I_1(\epsilon_o) = \int_O^T A(s) e^{-\mu(\epsilon_o)s} \Omega(s) ds. \tag{1}$$

In the above equation, A(s) is the absolute activity per unit volume at a depth s in the wall structure 10. The depth variable s is measured from the outer surface 11 of the wall structure 10 as shown in FIG. 1. At a depth s, $\Omega(s)$ is the solid angle projected through the collimator opening 18 and $\mu(\epsilon_o)$ is the attenuation coefficient of the wall structure 10 for gamma-rays of energy $\epsilon_o$. The solid angle $\Omega(s)$ is given by the equation:

$$\Omega(s) = \frac{1}{4\pi} \int \frac{dA}{r^2} = \frac{1}{4\pi} \int_O^{\alpha_1} r d\theta \int_O^{2\pi} \frac{r \sin\theta d\phi}{r^2},$$

where $\alpha_1 = \tan^{-1}(d/2x_1)$ is the half angle of the collimator, so that $$\Omega(s) = \frac{1 - \cos\alpha_1}{2}. \tag{2}$$

Since $\Omega(s)$ is independent of s and is a function of only the collimator property $\alpha_1$, it can be identified as $\Omega(\alpha_1)$.

The spatial dependence of the activity density A(s) has been previously shown to possess exponential behavior, as evidenced in the paper titled *LWR Pressure Vessel Dosimetry Improvement Program: PCA Experiments and Blind Test*, referenced above. Therefore, one can write the spatial activity density as $$A(s) = C e^{\lambda s}. \tag{3}$$

Here C is a constant, i.e., C=A(o), which represents the activity density at the surface and $\lambda$ is the neutron attenuation coefficient of the reactor pressure vessel. Using Equations (2) and (3) in Equation (1), one finds the quadrature result $$I_1(\epsilon_o) = \frac{C\Omega(\alpha_1)}{(\mu - \lambda)} [1 - e^{-(\mu-\lambda)T}]. \tag{4}$$

Using numerical estimates in Equation (4), one can show that the exponential term is negligible for many applications, in which case Equation (4) reduces simply to $$I_1(\epsilon_o) = \frac{C\Omega(\alpha_1)}{\mu - \lambda}. \tag{5}$$

The constants C and $\lambda$ of the parametric representation of activity density can be determined from Eqns. (4) or (5) in a number of ways. Equation (5) will be used in this treatment for the sake of simplicity. Since the more general treatment can be easily obtained from Equation (4) in an analogous fashion, only the results of this general treatment will be given.

The neutron attenuation coefficient $\lambda$ can be measured in separate benchmark field calibration experiments conducted relative to the tested object, such as the light water reactor-pressure vessel mockups studied in the pool critical assembly described in the referenced paper *LWR Pressure Vessel Dosimetry Improvement Program: PCA Experiments and Blind Test*. Using this value of $\lambda$, Equation (4) or (5) can be solved directly for C.

On the other hand, both parameters, C and $\lambda$ can be regarded as unknown, in which event an additional measurement is required. Consider therefore a second measurement with a different collimator of solid angle $\Omega(\alpha_2)$ which makes an angle $\theta$ with respect to the normal of the reactor pressure vessel surface. Using the above results, it can be shown for this case that $$I_2(\epsilon_o) = \frac{C\Omega(\alpha_2)}{(\mu - \lambda_2)} [1 - e^{-(\mu-\lambda_2)T_2}], \tag{6}$$

where $$\lambda_2 = \lambda \cos\theta, \tag{7a}$$

and $$T_2 = T/\cos\theta. \tag{7b}$$

Since $\lambda_2 \leq \lambda$, one again finds that the exponential term can be neglected for many applications so that $$I_2(\epsilon_o) = \frac{C\Omega(\alpha_2)}{\mu - \lambda_2}. \tag{8}$$

Taking the ratio of Eqn. (5) by Eqn. (8), one finds $$I_1(\epsilon_o)/I_2(\epsilon_o) = \left(\frac{\mu - \lambda_2}{\mu - \lambda}\right) \left(\frac{\Omega(\alpha_1)}{\Omega(\alpha_2)}\right),$$

which can be written in the form $$\frac{\mu - \lambda_2}{\mu - \lambda} = \delta, \tag{9a}$$

where $$\delta = \left(\frac{I_1(\epsilon_o)}{I_2(\epsilon_o)}\right) \left(\frac{\Omega(\alpha_2)}{\Omega(\alpha_1)}\right). \tag{9b}$$

The constant $\delta$ can be determined in terms of the SI(Li) gamma-ray spectrometer results, $I_1(\epsilon_o)$ and $I_2(\epsilon_o)$, obtained with the two different collimators. Consequently, use of Eqn. (7a) in Eqn. (9a) provides a relation that can be solved for $\lambda$. One finds $$\lambda = \mu \left(\frac{\delta - 1}{\delta - \cos\theta}\right). \tag{10}$$

This value of $\lambda$ can then be used in Eqn. (5) or Eqn. (8) to determine C.

The more general result, which follows from Eqns. (4) and (6), is $$\left(\frac{\mu - \lambda_2}{\mu - \lambda}\right) \left(\frac{1 - e^{-(\mu-\lambda)T}}{1 - e^{-(\mu-\lambda_2)T}}\right) = \delta, \tag{11}$$

where $\delta$ is again the constant given in Eqn. (9b). Equation (11) is a transcendental relation that can be solved for $\lambda$ iteratively. In fact, one would start the iterative process with the approximate solution given by Eqn. (10). Having determined $\lambda$ interatively, Eqns. (4) or (6) can be used to find C.

An additional point which must be stressed is the advantage of reduced background that arises for measurements conducted at an angle $\theta$ with respect to the normal to the reactor pressure vessel surface. Here the angle $\theta$ can be chosen so that the collimated spectrometer no longer directly views leakage radiation from the core that penetrates through the reactor pressure vessel. Consequently, measurements can be carried out with two different collimators which make angles $\theta_1$ and $\theta_2$, respectively, with respect to the normal to the reactor pressure vessel surface. Under these conditions, one has $$I_1(\epsilon_o) = \frac{C\Omega(\alpha_1)}{\mu - \lambda_1}[1 - e^{-(\mu - \lambda_1)T_1}], \quad (12)$$

and $$I_2(\epsilon_o) = \frac{C\Omega(\alpha_2)}{\mu - \lambda_2}[1 - e^{-(\mu - \lambda_2)T_2}]. \quad (13)$$

Using these results, Eqns. (10) and (11) generalize to $$\lambda = \mu\left(\frac{\delta - 1}{\delta \cos\theta_1 - \cos\theta_2}\right), \quad (14)$$

and $$\left(\frac{\mu - \lambda_2}{\mu - \lambda_1}\right)\left(\frac{1 - e^{-(\mu - \lambda_1)T_1}}{1 - e^{-(\mu\lambda_2)T_2}}\right) = \delta, \quad (15)$$

respectively. Here $\delta$ is again given by Eqn. (9b) and $$\left.\begin{array}{l}\lambda_1 = \lambda \cos\theta_1 \\ \lambda_2 = \lambda \cos\theta_2 \\ T_1 = T/\cos\theta_1 \\ T_2 = T/\cos\theta_2\end{array}\right\} \quad (16)$$

One can easily show that Eqns. (14) and (15) obey the correct limiting condition for $\theta_1 \rightarrow 0$, thereby reducing to Eqns. (10) and (11), respectively. As before, the solution of $\lambda$ given by Eqn. (14) can be used in the approximations obtained from Eqns. (12) or (13), i.e., when the exponential term is neglected in these equations, to provide C. In an analogous manner, the more general result can be obtained by using the iterative solution of $\lambda$ found from Eqn. (15), in either Eqn. (12) or (13) to provide C.

Actually, in-situ gamma-ray continua in reactor environments possess many peaks which are observed above the general level of the continuum. Furthermore, there is no restriction on the number of different peaks which can be analyzed for absolute activity density. Since these different peaks arise from neutron reactions with the constituent isotopes of the reactor pressure vessel, or for measurements from inside the vessel, stainless steel and iron constituents of the core barrel, thermal shield, and/or cladding on the reactor pressure vessel wall surface 12, the potential exists not only for determination of neutron exposure fluence, but energy spectral information as well. All these data can be used in unfolding or least squares adjustment codes in the same way radiometric dosimetry is customarily analyzed.

Finally, it must be noted that limitations on accessibility do exist for the collimated Si(Li) spectrometer. For certain reactor designs, the reactor cavity is too small to permit insertion of the collimated spectrometer detector. On the core side, the thermal shield, pad or barrel may lie between the collimated spectrometer detector, and the reactor pressure vessel. In this case, the method is actually applied to the specific configuration viewed by the collimator. Often one can insert the collimated Si(Li) spectrometer detector in reactor instrument tubes which allow a clear view of the reactor pressure vessel. The advantage of viewing the bare reactor pressure vessel surface lies in an improved signal to background ratio for the quantification of activity within the reactor pressure vessel. Moreover, neutron dosimetry for the reactor pressure vessel can be performed without the need for extrapolation.

In addition to the determination of neutron exposure, the same non-destructive method can be used to determine the concentrations of different constituents in the object by measuring the absolute flux of characteristic gamma-rays from radioactivity induced into these constituents by the neutron exposure. For example, the concentration of copper, as earlier noted, is a crucial variable governing the radiation induced embrittlement of reactor pressure vessel steels. Hence, copper concentraion is a critical factor in end-of-life determinations for nuclear power reactor pressure vessels (PV). Copper concentration is not only important in PV base metals, but is of particular significance in PV weldments.

The same equipment and procedures for neutron exposure determinations described above can be used to determine the copper concentration of PV base metals and weldments. To determine such PV copper concentrations, measurements would have to begin soon after power reactor shutdown. Two radionuclides are produced by neutron capture on natural copper, namely $^{64}$Cu and $^{66}$Cu. While the short half-life of $^{66}$Cu, only about 5.1 minutes, makes this radionuclide impractical to use in this application, $^{64}$Cu possesses a 12.7 hour half-life and consequently can be used for PV observations. In a few hours after shutdown, the collimated Si(Li) Compton spectrometer can be assembled for measurement of PV gamma spectra.

Two candidate gamma-rays exists in the $^{64}$Cu decay, namely the 1.346 MeV transition from the low intensity electron capture branch (0.6%) and annihilation radiation at 0.511 MeV from the positron decay branch (19%). The foregoing neutron exposure analysis for peak intensities above the general level of the gamma continum will also be applicable for these two gamma-rays from $^{64}$Cu.

Gamma-ray peaks due to the decay of $^{59}$Fe will exist in the very same spectral measurements. The $^{59}$Fe radionuclide (45.5 day half-life) is produced by neutron capture on natural iron, wherein $^{58}$Fe exists at a level of 0.3 percent. Two candidate peaks from $^{59}$Fe exist, namely the transition at 1.292 MeV (45%) and the transition at 1.099 MeV (53%). Again using the neutron exposure analysis given above, the absolute $^{59}$Fe activity per unit volume A(s) can be quantified. Consequently, using equation (3), one can write for the $^{64}$Cu activity per unit volume $$A_1(s) = C_1 e^{\lambda s}, \qquad (17)$$

and for the $^{59}$Fe activity per unit volume $$A_2(s) = C_2 e^{\lambda s}. \qquad (18)$$

The $^{64}$Cu and $^{59}$Fe activities per unit volume at a depth s can be simply expressed in terms of the thermal neutron flux [neutrons/(cm$^2$·sec)], $\phi_{th}(s)$, at depth s. One has $$A_1(s) = \phi_{th}(s) \cdot \sigma_1 \cdot \rho_1 \cdot e^{-\lambda_1 t_d} (1 - e^{-\lambda_1 t_x}), \qquad (19)$$

and $$A_2(s) = \phi_{th}(s) \cdot \sigma_2 \cdot \rho_2 \cdot e^{-\lambda_2 t_d} (1 - e^{-\lambda_2 t_x}). \qquad (20)$$

Here:

$\lambda_1$ is the $^{64}$Cu decay constant
$\lambda_2$ is the $^{59}$Fe decay constant
$\sigma_1$ is the $^{63}$Cu thermal neutron capture cross section
$\sigma_2$ is the $^{58}$Fe thermal neutron capture cross section
$\rho_1$ is the $^{63}$Cu concentration (atoms/cm$^3$)
$\rho_2$ is the $^{58}$Fe concentration (atoms/cm$^3$)
$t_x$ is the duration time of the irradiation
$t_d$ is the elapsed time since reactor shutdown.

All these parameters are known except for the $^{63}$Cu concentration $\rho_1$. Hence taking the ratio of Equation (19) to Equation (20), one can write $$\rho_1/\rho_2 = K, \qquad (21)$$

where K is expressed in terms of known parameters as $$K = \frac{A_1(s) e^{\lambda_1 t_d}(1 - e^{-\lambda_2 t_x}) \sigma_2}{A_2(s) e^{\lambda_2 t_d}(1 - e^{-\lambda_1 t_x}) \sigma_1}. \qquad (22)$$

Finally, the copper concentration can be simply obtained from the $\rho_1/\rho_2$ ratio by using the known percent abundances of $^{63}$Cu and $^{58}$Fe in natural copper and iron, respectively.

The copper concentration of the base metal can often be determined from archive PV specimens, so that only the copper concentration of PV weldments is desired for certain power reactors. In this case one can use Equations (21) and (22) to show that only relative gamma spectra observations are necessary between PV base metal and PV weldments. To this end, using Equations (17) and (18) in Equation (22) yields $$K = \frac{C_1 e^{\lambda_1 t_d}(1 - e^{-\lambda_2 t_x}) \sigma_2}{C_2 e^{\lambda_2 t_d}(1 - e^{-\lambda_1 t_x}) \sigma_1}. \qquad (23)$$

Now from Equations (12) and (13), one can write $$C_1 = k_1 I_1, \qquad (24)$$

and $$C_2 = k_2 I_2. \qquad (25)$$

Here $k_1$ and $k_2$ are constants depending on the collimator, the angle of view, and the energy of the particular gamma-ray peak in question. The constants $k_1$ and $k_2$ can have different form depending upon whether the exact solution of Equations (12) and (13) have been used or the approximations of Equations (5) and (8) are used. However, the particular form that is chosen for $k_1$ and $k_2$, i.e., whether exact solution or approximation, does not effect the resulting analysis.

Hence using Equations (24) and (25) in Equation (23), one can write $$K = N \cdot (I_1/I_2), \qquad (26)$$

where N is a constant given by $$N = \frac{k_1 e^{\lambda_1 t_d}(1 - e^{-\lambda_2 t_x}) \sigma_2}{k_2 e^{\lambda_2 t_d}(1 - e^{-\lambda_1 t_x}) \sigma_1}. \qquad (27)$$

Consequently, Equation (21) becomes $$(\rho_1/\rho_2) = N \cdot (I_1/I_2), \qquad (28)$$

The collimated Si(Li) spectrometer can be applied for both PV base metal and PV weldment gamma spectra observations. In this event, Equation (28) can be used for both measurements so that one can write $$(\rho_1/\rho_2)_{weld} = N \cdot (I_1/I_2)_{weld}, \qquad (29)$$

and $$(\rho_1/\rho_2)_{base\ metal} = N \cdot (I_1/I_2)_{base\ metal}. \qquad (30)$$

The ratio of Equation (29) to Equation (30) yields $$(\sigma_1/\sigma_2)_{weld} = \frac{(I_1/I_2)_{weld}}{(I_1/I_2)_{base\ metal}} \cdot (\sigma_1/\sigma_2)_{base\ metal}. \qquad (31)$$

Hence, if the copper concentration is known for the base metal, then only relative Si(Li) gamma spectra observations are needed between the base metal and weldment to determine the copper concentration of the weldment.

Interferences and background can arise in PV gamma spectra observed with the collimated Si(Li) Compton spectrometer. Additional radionuclides are produced which possess gamma-ray transitions that are close to the gamma-ray energies emitted by either $^{64}$Cu or $^{59}$Fe. For example, $^{58}$Co can be produced by an (n,p) reaction on $^{58}$Ni. Since $^{58}$Co is a positron emitter, annihiliation radiation would be produced at 0.511 MeV from the $^{58}$Co decay just as it is produced in the decay of $^{64}$Cu. However the $^{58}$Ni(n,p)$^{58}$Co reaction cross section is very small relative to the $^{63}$Cu (n,p) cross section and the $^{58}$Co half-life is 70.8 days, which is considerably longer than the 12.7 hr. half-life of $^{64}$Co. Hence, the background annihilation component from $^{58}$Co will be small relative to the $^{64}$Cu annihilation gamma peak.

In general, the time-dependent decay of the different radionuclides contributing to a given gamma peak can be used to separate signal from background. For example, that component of peak intensity at the annihilation energy possessing a 12.7 hr. half-life can be determined by measuring time-dependent PV gamma spectra. Sequential gamma spectra measurements over a time period of a few days should serve to isolate the 12.7 hr decay component that can be uniquely attributed to $^{64}$Cu.

Another example of background is the production of $^{60}$Co in the PV by neutron capture on trace concentrations of natural cobalt, i.e., $^{59}$Co. The $^{60}$Co decay possesses gamma-ray transitions at 1.173 MeV (100%) and 1.332 MeV (100%). Since the energy resolution of the Si(Li) spectrometer is about 30 keV (FWHM), the 1.332 MeV gamma-ray from $^{60}$Co would interfere with the 1.346 MeV transition of $^{59}$Fe. Fortunately, $^{60}$Co has a half-life of 5.27 yr so that time-dependent measurements can be used to separate signal from background should the need arise.

There exists another general method for isolating background contributions that must be stressed. It is based on the observation of additional peaks in the gamma spectrum that are emitted by the very same background producing radionuclide. If such a peak can be identified, then the absolute activity of the background radionuclide can be quantified. Knowledge of the decay scheme of this background radionuclide together with the absolute activity of the background radionuclide provide the means to determine the background contribution to the peak intensity in question. For example, $^{58}$Co possesses a gamma transition at 0.8108 MeV (99%.). Consequently, if the $^{58}$Co decay is contributing to the annihilation peak at 0.511 MeV, then a peak in the gamma spectrum whould be observed at 0.8108 MeV. Hence, observation of this peak at 0.8108 MeV with the collimated Si(Li) spectrometer can be used to quantify the absolute activity per unit volume of $^{58}$Co. This absolute $^{58}$Co activity together with a knowledge of the $^{58}$Co decay scheme will permit evaluation of the background component at the 0.511 MeV annihilation gamma-ray energy.

For some applications, particularly for measurements that might be made on the inside surface of a PV, some account would have to be taken of differences between thermal and fast neutron induced activations in Cu and Fe. Generally, this should involve only a small correction to the thermal neutron induced events.

This method for determination of constituent concentrations is nondestructive and possesses a number of additional advantages. Copper concentrations can be determined locally as a function of spatial position on the PV surface, so that base metal and weldment copper concentrations can be measured. The exact location of a weld of interest need not be known, since the change in gamma spectra between the base metal and weldment can be used to locate the collimated spectrometer at the weld. If the copper concentration of the base metal is known, then only relative gamma spectra measurements between base metal and weldment are needed to determine the copper concentration of the weldment. Copper concentrations are determined without the need to quantify the thermal neutron exposure flux $\phi_{th}$.

While it was convenient to use copper, because of its significance in pressure vessel base metals and weldments, as an example in describing the non-destructive method for determining constituent concentrations, it should be understood that this aspect of the invention is not restricted thereto, but has utility in measuring the concentration of any of the several constituents found in irradiated objects of interest.

In carrying out the method physically, whether for neutron exposure or constituent concentration determinations, the detector 13 views the exposed surface 11 on the object or wall structure 10, through the collimator opening 18, which is maintained at a preselected angle relative to the surface area facing it. As the shielded detector 13 traverses the surface area 11, peaks in the continuous spectrum of detected gamma-rays at different energy levels are electronically measured. From these values, a record can be made of the resulting flux density peak values of the gamma-rays at various energy levels, and a selection can be made of one or more flux density peak values at energy levels characteristic of the gamma-ray radiation that results following neutron exposure of an object. The spatial activity density of such radiation can be identified through the above-described mathematical relationships. This might require a second scanning step using a modified shield configuration or the repositioning of the angular relationship between the collimator opening 18 and the scanned surface 11, or a sequential set of measurements over a given time period. After the spatial activity density value has been identified, known deductive relationships can be utilized to determine the spatial and angular dependence of neutron exposure or th spatial constituent concentration at the regions of interest in the object being tested.

To determine the spatial and angular dependence of the neutron exposure, unfolding methods based on least squares analysis can be applied. ASTM Standard E944, "Application of Neutron Spectrum Adjustment Methods," describes procedures that can be used to deduce neutron exposure from activation and/or reaction rate measurements. A neutron transport calculation (E482 "Application of Neutron Transport Methods for Reactor Vessel Surveillance, Test Results Extrapolation") is performed for the object under study and the calculated neutron energy spectrum is used as input to a least squares adjustment code together with the absolute spatial activity density. The least squares adjustment code then produces an absolute neutron exposure energy spectrum that is consistent with the observed activity density.

This least squares analysis procedure can be repeated at points (throughout the object under study) where the spatial activity density has been measured by continuous gamma-ray spectrometry. In this way, the spatial and angular dependence of the neutron exposure is determined.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A portable, non-destructive method for determination of the spatial distribution of neutron exposure to which a selected object has been subjected, comprising the following steps:

exposing the shielded detector of a spectrometer to a limited portion of a surface area of the object through a small diameter collimator opening directed toward the surface area;

electronically measuring the continuous spectrum of detected gamma-rays at different energy levels during a traverse of the surface area by the shielded detector;

recording a flux density peak value of the gamma-rays at a selected energy level characteristic of neutron exposure;

identifying a relationship between the flux density peak value and the spatial activity density for the measured gamma-rays; and subsequently deriving spatial and angular information concering neutron exposure across the surface area of the object by known relationships to the identified spatial activity density value.

2. A method as set out in claim 1, wherein the spatial activity density value is related to a neutron attenuation coefficient value measured by an independent measurement technique.

3. A method as set out in claim 1, wherein a second measurement of detected gamma-rays is utilized to identify the desired relationship between the flux density peak value and the spatial activity density value for the measured gamma-rays.

4. A portable non-destructive method for determination of the neutron exposure to which a selected surface area on a object has been subjected, comprising the following steps:

exposing the solid state lithium-drifted silicon detector of a Compton Recoil Gamma-Ray Spectrometer to a limited portion of the surface area of the object through a small diameter collimator opening directed toward the surface area;

electronically measuring the continuous spectrum of detected gamma-rays at different energy levels during a first traverse of the surface area by the shielded detector;

recording a first flux density peak value of the gamma-rays at a selected energy level characteristic of neutron exposure;

identifying a first relationship between the first flux density peak value and the spatial activity density value for the measured gamma-rays;

modifying the exposure of the detector to the surface area;

electronically measuring the continuous spectrum of detected gamma-rays at different energy levels during a second traverse of the surface area by the detector;

recording a second flux density peak value of the gamma-rays at the previously selected energy level;

identifying a second relationship between the second flux density peak value and the spatial activity density value;

solving the first and second relationships to identify the spatial activity density value of the gamma-rays at the characteristic energy level; and subsequently deriving information concerning spatial and angular neutron exposure of the object by known relationships to the identified spatial activity density value.

5. A portable, non-destructive method for determining constituent concentrations of a selected irradiated object comprising the following steps:

exposing the detector of a spectrometer to a limited portion of the surface area of the object through a small diameter collimator opening directed toward the surface area;

electronically measuring the continuous spectrum of detected gamma-rays at different energy levels during a traverse of the surface area by the shielded detector;

recording a flux density peak value of the gamma-rays at a selected energy level characteristic of neutron exposure;

identifying a relationship between the flux density peak value and the spatial activity density for the measured gamma-rays; and subsequently deriving information concerning the spatial constituent concentrations across the surface area of the object by known relationships to the identified spatial activity density value.

6. A method as set out in claim 5, including taking a sequential series of measurements over a given time period.

7. A method as set out in claim 5, wherein the flux density peak value of the gamma-rays from a specific constituent is identified to determine the concentration of said specific constituent in said object by known deductive relationships.

8. A method as set out in claim 7, wherein said specific constituent is copper.

9. A method as set out in claim 6, wherein said series of measurements are taken with one detector and collimator arrangement.

10. A method as set out in claim 6, wherein said series of measurements are taken with a plurality of detector and collimator arrangements.

* * * * *